US006041125A

United States Patent [19]

Nishimura et al.

[11] Patent Number: 6,041,125

[45] Date of Patent: *Mar. 21, 2000

[54] ACTIVE ACOUSTIC WALL

[75] Inventors: Masaharu Nishimura; Keizo Ohnishi; Chiaki Yasuda; Shinichiro Kajii, all of Takasago, Japan; William P. Patrick; Anthony C. Zander, both of East Hartford, Conn.

[73] Assignees: Mitsubishi Jukogyo Kabushiki Kaishal, Tokyo, Japan; United Technologies Corporation, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/769,381

[22] Filed: Dec. 19, 1996

[30] Foreign Application Priority Data

Aug. 15, 1996 [JP] Japan .................................... 8-215685

[51] Int. Cl.[7] ...................................................... A61F 11/06

[52] U.S. Cl. ......................................... 381/71.4; 381/71.1

[58] Field of Search ................................. 381/71.1, 71.7, 381/71.14, 71.3, 71.4, 71.5, 71.8, 72; 181/206

[56] References Cited

U.S. PATENT DOCUMENTS

| | | | |
|---|---|---|---|
| 5,119,427 | 6/1992 | Hersh et al. | 381/71.14 |
| 5,574,264 | 11/1996 | Takemori et al. | 181/206 |
| 5,598,479 | 1/1997 | Dodt et al. | 381/71.7 |
| 5,627,897 | 5/1997 | Gagliardini et al. | 381/71.7 |

FOREIGN PATENT DOCUMENTS

| | | |
|---|---|---|
| 0 481 450 | 4/1992 | European Pat. Off. . |
| 0 665 529 A2 | 8/1995 | European Pat. Off. . |
| WO 94/05005 | 3/1994 | WIPO . |
| WO 95/19075 | 7/1995 | WIPO . |

OTHER PUBLICATIONS

Acustica, vol. 81 (1995), pp. 356–363, R. Lippold et al., "Acoustic Absorption in Ducts with an Actively Controlled Wall Admittance" (English summary).

Acustica, vol. 81 (1995), pp. 421–432, R. Lippold, "Design of Absorption Silencer with Active Wall Admittance" (English summary).

1997 Acoustical Society of America, Mar. 1997, pp. 1512–1515, Samson Beyene et al., A New Hybrid Passive/Active Noise Absorption System.

(List continued on next page.)

*Primary Examiner*—Vivian Chang

*Attorney, Agent, or Firm*—Wenderoth, Lind & Ponack, L.L.P.

[57] ABSTRACT

An active acoustic wall has sound-pressure detectors provided within respective cells so that a detected signal acts to oscillate an oscillation plate in the cell. A porous material on a surface is thereby provided with a high sound absorption coefficient over a wide frequency range. A space between a porous material or a perforated plate 1 on the surface and a back material fixed on a back side is divided into a plurality of sections so as to form cells 10 containing an air layer or a porous sound-absorbing material. Oscillation plates 6 are arranged within respective cells 10 so as to be driven for oscillation by oscillation-plate driving units 5. Sound-pressure detectors 7 are provided close to the porous material 1 in the cell 10 so that a detected signal is inputted to a signal-processing unit 8. The signal processing unit 8 outputs a signal to the driving unit 5 for oscillating the oscillation plate 6 such that an output of the sound-pressure detector is minimized. The sound pressure on the surface of the porous material 1 is minimized at all frequencies. The velocity of particles on the surface becomes large so that the particles are turned into thermal energy, thereby providing a high sound-absorption coefficient.

32 Claims, 11 Drawing Sheets

OTHER PUBLICATIONS

Journal of Vibration, Acoustics, Stress, and Reliability in Design, vol. 106, Jul. 1984, pp. 389–392, D. Guicking et al., "An Active Sound Absorber with Porous Plate".

Journal of Vibration, Acoustics, Stress, and Reliability in Design, vol. 106, Jul. 1984, pp. 393–396, D. Guicking et al., "Active Impedance Control for One–Dimensional Sound".

"A New Filtering Method by Feedback for A.N.C. at the Ear", pp. 1083, Ch. Carme Laboratoire de Mécanique et d'Acoustique du C.N.R.S.

Acustica, vol. 69 (1989), pp. 175–184, M. Möser, "Active Control of Simple Self–Excited Resonators" (English summary).

Smart Mater. Struct. 3 (1994), pp. 18–25, Denis Thenail et al., "Active Enhancement of the Absorbent Properties of a Porous Material".

Internoise, Jul. 10–12, 1995, pp. 481–484, Vér et al., "Active Liner System for Jet Engine Exhaust Silencers".

Pi: INCIDENT SOUND PRESSURE ON A POINT X = −H

Pr: REFLECTING SOUND PRESSURE ON A POINT X = −H

Pc: CONTROLLING SOUND PRESSURE RADIATED FROM THE OSCILLATION PLATE ON A POINT X = −H

Pi: INCIDENT SOUND PRESSURE

Pr: REFLECTIVE SOUND PRESSURE WHEN THE OSCILLATION PLATE IS RIGID

Pc: RADIATIVE SOUND PRESSURE CREATED BY OSCILLATION WITH THE OSCILLATION PLATE

ACTIVE ACOUSTIC WALL

BACKGROUND OF THE INVENTION

This invention relates to acoustic, sound-absorbing nacelles or casings which are applied for aircraft jet-engines, fans, or compressors, etc. and more particularly to an active acoustic wall applicable for ordinary sound arresters or sound-absorbing room walls.

There are illustrated in FIGS. 20 to 23 structural views of conventional acoustic walls. In FIG. 20, 41 is a surface porous material, 42 are air layers, 43 are partition plates, and 44 is a back wall as a fixing section. An acoustic wall is constituted, as shown, by the porous material 41 provided on a surface thereof, a plurality of the partition plates 43 dividing an interior thereof to provide the air layers 42, and the back wall 44 onto which these elements are fixed.

Examples for acoustic walls are given, i.e., no porous material are used in the surface in FIG. 21, a perforated plate 52 having a plurality of perforations 52*a* is employed instead of the surface porous material 41 in FIG. 22, and a sound-absorbent material 45 is filled in place of the air layers 42 in FIG. 23.

SUMMARY OF THE INVENTION

In the aforesaid acoustic walls, the thickness H of the acoustic wall and the flow resistance for the porous material on the surface thereof are selectively determined so that the surface impedance is optimized by tuning to provide a high sound-absorption coefficient in a specified frequency range. However, it is generally difficult to increase the sound-absorption coefficient in a low-frequency range, because even if it be optimized at a certain specified frequency then other frequencies will naturally be fallen out of the optimization. For instance, the perfect sound absorption for a frequency of 100 Hz requires a thickness of approximately 850 mm for the wall, which is extremely and impractically thick.

It is therefore the object of the invention to realize an active acoustic wall, which is adapted to oscillate oscillation plates thereof to provide the optimization in impedance for absorbing sound with a high sound-absorption coefficient over a low-to-high, wide frequency range.

Therefore, the present invention provides means set forth hereinbelow.

(1) An active acoustic wall comprising:

- a perforated plate provided on a surface thereof, which is formed by a perforated member having a plurality of perforations, a porous material or both of them;
- a back wall provided on the back side of said perforated plate;
- partition plates dividing the spacing between said perforated plate and said back wall into a plurality of sections;
- oscillation plates respectively provided within said sections;
- driving units of driving said oscillation plates;
- sound-pressure detectors respectively provided inside or on the surface of said perforated plate, or inside each oscillation plate, or at a desired location within said sections divided by said partition plates; and
- a signal processing unit for controlling oscillation of said oscillation plates in a manner such that sound absorption at the desired location is made on the basis of the output from the sound-pressure detectors.

(2) An active acoustic wall according to (1), wherein absorption materials are filled in said plurality of the sections.

(3) An active acoustic wall according to (1) or (2), wherein said partition plates are all eliminated and the sections become a continuous space.

(4) An active acoustic wall according to (1), (2) or (3), wherein said oscillation plate and said back wall are integrally formed.

(5) An active acoustic wall according to (1), (2), (3) or (4), wherein said perforated plate is omitted to open the surface.

(6) An active acoustic wall according to (1), (2), (3) or (4), wherein said signal processing unit operates on controlling the oscillation of each oscillation plate in a manner such that a surface impedance of said perforated plate calculated on the basis of the output from each sound-pressure detector approximates to a predetermined value.

(7) An active acoustic wall according to (1), (2), (3), (4) or (5), wherein said signal processing unit operates on controlling the oscillation of each oscillation plate in a manner such that the output from each sound-pressure detector approximates to a minimum value.

(8) An active acoustic wall according to (1), (2), (3), (4) or (5), wherein said signal processing unit operates on controlling the oscillation of each oscillation plate in a manner such that a characteristic of a one-loop transfer function in which transfer is made through a sound pressure generated by the oscillation of each oscillation plate to the output of the sound-pressure detector approximates to −1.

(9) An active acoustic wall according to (1), (2), (3), (4) or (5), wherein two sound-pressure detectors for separating an incident sound wave from a reflecting sound wave and measuring said waves respectively are provided within each section, and said signal processing unit operates on controlling the oscillation of each oscillation plate in a manner such that a reflectivity of the sound wave calculated on the basis of the output from said two sound-pressure detectors approximates to a predetermined value.

Then, the operation will be explained in detail concerning the principal of this invention with reference to FIGS. 12 to 14. In an acoustic wall having a rigid back wall 4 shown in FIG. 12, when a sound frequency is at a value wherein the thickness H of the acoustic wall falls on an odd number of times a quarter sound wavelength, the sound mode $M_1$ comes to the minimum and the particle velocity mode $M_2$ is at the maximum in the vicinity of a surface porous material. Consequently, if the flow resistance of the surface porous material 1 is set appropriately, the movement of particles is converted by the surface resistance into a thermal energy, thereby presenting a high sound-absorption coefficient.

On the contrary, the sound absorption coefficient lowers significantly, when the frequency lies in a low range where the particle velocity mode $M_2$ is small or in such a value that the thickness H is even number of times a quarter wavelength where the particle velocity mode $M_2$ presents a node. This state is shown in FIG. 13, wherein the sound-absorption coefficient, where the thickness H is a quarter wavelength, drops at frequencies $2f_0$, $4f_0$, $8f_0$.

To this end, if the back wall per se or the oscillation plate provided in front thereof is caused oscillation matched to an incident sound wave such that the sound pressure in the vicinity of the surface porous material is controlled at all times to "0" at every frequency of a sound wave, then the velocity of particles neighboring thereto becomes the maximum to offer a high sound-absorption coefficient over entire range of frequencies.

The relationship set forth above will be explained with expressing by equations. In FIG. 14, provided that incident sound pressure on a point x is $P_i$, the particle velocity thereof is $U_i$, the reflecting sound pressure is $P_r$, the particle velocity thereof is $U_r$, the controlling pressure of sound radiated from the oscillation plate 4 is $P_c$, the particle velocity thereof is $U_c$, the gas density is ρ, the sound velocity is C, and k is a constant, then the relationship is expressed by Equation (1) given hereinbelow.

$$P_i = P_{io}e^{i(\omega t-kx)},\quad U_i = \frac{P_{io}}{\rho C}e^{i(\omega t-kx)} \tag{1}$$
$$P_r = P_{ro}e^{i(\omega t+kx)},\quad U_r = -\frac{P_{ro}}{\rho C}e^{i(\omega t+kx)}$$
$$= P_{io}e^{i(\omega t+kx)} \qquad = -\frac{P_{io}}{\rho C}e^{i(\omega t+kx)}\ (Q\,P_{io} = P_{ro})$$
$$P_c = P_{co}e^{i(\omega t+kx)},\quad U_c = -\frac{P_{co}}{\rho C}e^{i(\omega t+kx)}$$

From the above, the sound pressure P and the particle velocity at the point x can be represented as Equation (2).

$$P = P_i + P_r + P_c \tag{2}$$
$$= \{P_{io}(e^{-ikx} + e^{ikx}) + P_{co}e^{ikx}\}e^{i\omega t}$$
$$U = U_i + U_r + U_c$$
$$= \frac{1}{\rho C}\{P_{io}(e^{-ikx} - e^{ikx}) - P_{co}e^{ikx}\}e^{i\omega t}$$

The surface impedance at x=−H is given by Equation (3).

$$\zeta = \frac{1}{\rho C}\left(R_f + \frac{P}{U}\right) \tag{3}$$

In equation (3), $R_f$ is the flow resistance for the surface porous material. Also, the sound absorption coefficient α is expressed as Equation (4).

$$\alpha = 1 - \left|\frac{1-\zeta}{1+\zeta}\right|^2 \tag{4}$$

Accordingly, if control is made to fulfill Equation (5), the value P=0 is obtained from Equation (2). Further, if the flow resistance for the surface porous material is determined to meet the relation $R_f \approx \rho C$, the value ζ≈1 is obtained because P=0. If this ζ≈1 is substituted in Equation (4), then α≈1 is obtained and the absorption coefficient becomes approximately 1.

$$P_{co} = -P_{io}\frac{e^{ikH} + e^{-ikH}}{e^{-ikH}} \tag{5}$$

Now, if an approximation of α>0.5 is expected to obtain, then a relation 0.17<ζ<6 is given so that the flow resistance $R_f$ may be 0.17 ρC<$R_f$<6ρC.

The above-stated control, which is presented by P=0 at x=−H in Equation (5), may be embodied by employing an existing active control techniques such as feed-forward control, feed-back control, and the like.

The means (1) of the invention makes control as stated above by dividing the spacing between the surface porous plate and the back-side back wall into a plurality of sections, arranging oscillation plates and sound-pressure detectors closed to the porous plate within the respective sections, inputting an output signal detected by the sound-pressure detector to the signal processing unit where the signal is subjected to processing, as stated in (7), to thereby cause the oscillation plate to oscillate such that the output of the sound-pressure detector is minimized by attaining P=0 at x=−H.

The present invention is applicable to a variety of specifications for acoustic walls in which the perforated plate is provided by using a perforated member having a plurality of perforations formed therein, or a porous material, singly or in combination.

The operations of the means (8) of the invention will then be explained in detail based on reference to FIGS. 15 and 16. As shown in FIG. 15, if the sound pressure is P which is detected by the sound-pressure detector 7 placed just in front of the oscillation plate, then it can be expressed as Equation (6), $$P=P_i+P_r+P_c \tag{6}$$

where $P_i$ is incident sound pressure, $P_r$ is reflective sound pressure obtainable when the oscillation plate being rigid, and $P_c$ is radiative sound pressure created by oscillation with the oscillation plate. Now, if a one-loop transfer function is G, wherein transfer is made from the sound-pressure detector 7 via the signal-processing unit 8, the driving unit 5, the oscillation plate 6, and back in a sound-wave form to the sound-pressure detector 7, Equation (6) is rewritten as Equation (7).

$$P_c = GP \qquad \therefore (1-G)P = P_i + P_r \tag{7}$$
$$P = \frac{P_i + P_r}{1-G}$$

In this case, if the sound-pressure detector 7 is placed sufficiently close to the oscillation plate 6 with respect to a sound wavelength, then the relation $P_r \approx P_i$ is obtained. That is, Equation (7) is transformed into Equation (8).

$$P = \frac{2P_i}{1-G} \tag{8}$$

On the other hand, if the sound-pressure reflectivity is r, P is given by Equation (9).

$$P=P_i+rP_i=(1+r)P_i \tag{9}$$

Equation (10) is obtained from Equations (8) and (9) above.

$$(1+r)P_i = \frac{2P_i}{1-G} \quad \therefore r = \frac{1+G}{1-G} \tag{10}$$

The absorption coefficient α, on the other hand, is obtained from Equation (11), $$\alpha = 1 - |r|^2 = 1 - \left|\frac{1+G}{1-G}\right|^2 \tag{11}$$

where G is a complex number, and the relation between G and r, α is given as shown in FIG. 16. That is, the perfect sound absorption is achieved when α=1 stands at G=−1 (gain 1, phase inverted), so that a comparatively high sound-absorption coefficient is obtainable on a side where the gain exceeds 1 with the phase inverted. In other words, when the one-loop transfer function is adjusted so as to meet the above, the reflective sound pressure $P_r$ by a rigid wall is canceled by the controlling sound pressure $P_c$ to be eliminated, thereby realizing perfect sound absorption.

In the means (8) of the invention, the control on the transfer function G is made as stated above. That is, the spacing between the surface-side porous plate and the back-side back wall is divided into a plurality in number, the oscillation plates and the sound-pressure detectors close to the porous plate are arranged within respective sections, an output obtained through detection by the sound-pressure detector is inputted to the signal processing unit where it is subjected to signal-processing to cause the oscillation plate to oscillate, wherein control is made such that the characteristic of a one-loop transfer function unlimitedly nears toward −1 (gain 1, phase inverted).

In the means (5), the perforated plate is omitted to open the surface, in the means (3) the partition plate is removed away, in the means (4) the sound-pressure detectors and the back wall are integrally incorporated, and the perforated plate is provided by a perforated member formed with a plurality of perforated or a porous material, singly or in combination.

Then, the operation of the means (6) and (9) will be explained. In the means (6), an oscillation plate is arranged within an air layer or a sound-absorbent material so that the oscillation plate is oscillated in a manner such that the surface impedance becomes optimal for an incident sound wave. As stated in (9), the surface porous material serves as resistance to the surface impedance. Therefore, the surface impedance can be easily optimized by appropriately selecting the flow resistance. In this case, if two sound-pressure detectors are arranged along a direction perpendicular to the wall, it is possible to measure separately an incident wave and a reflected wave to thereby permit the calculation therefrom on the reflectivity. Thus, the oscillation plate can be controlled so as to bring the reflectivity to an optimal value.

The similar effect is also provided as by the means (2), wherein the air layer is filled with a sound-absorbent material. Incidentally, in this case, an obliquely-incident sound wave significantly attenuates in level, which may allow the omission of partition plates. The similar effect is also expected by the means (3) in which the perforated plate is removed to open the surface there.

Where a sound wave in a flat-plane form is incident onto a rigid wall, the sound wave will be reflected perfectly. Such sound wave, however, can be also adjusted desirably of its reflectivity by appropriately causing oscillation in the wall in accordance with a frequency of the coming sound wave as in the means (4).

As explained in detail above, an acoustic wall according to the present invention is basically characterized by comprising:

a perforated plate provided on a surface thereof;

a back wall provided on the back side of the perforated plate;

partition plates dividing the spacing between the perforated plate and the back wall into a plurality in number;

oscillation plates respectively provided in the sections;

driving units for driving the oscillation plates;

sound-pressure detectors respectively provided inside or on the surface of said perforated plate, or inside each oscillation plate, or at a desired location within said sections divided by said partition plates; and a signal processing unit for performing signal processing by the use of a detected signal given from a sound-pressure detector to output a signal so that a driving unit is driven to oscillate oscillation plate.

Therefore, the present invention provides a high sound-absorption coefficient over a low-to-high wide frequency range.

DETAILED DESCRIPTION OF THE PREFERRED EMBODIMENTS

Figure 1:
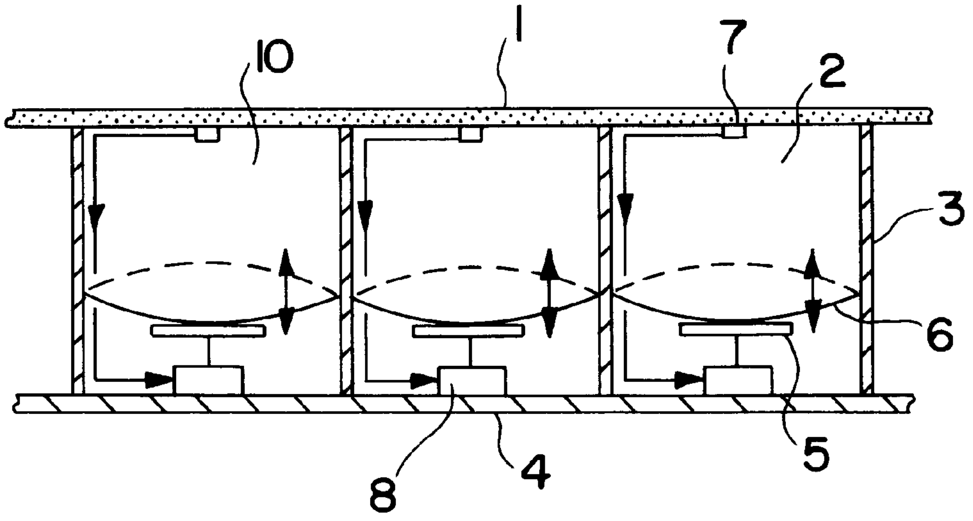
FIG. 1 is an structural view of an active acoustic wall according to a first embodiment of the invention.

The invention will now be explained on preferred embodiments based referring to on the drawings. FIG. 1 is a structural view of an acoustic wall according to a first embodiment of the invention, wherein a porous material 1 is given on a surface thereof which may be formed by a porous material, a perforated plate, or both of them. Reference character 4 represents a back wall, and 3 are a plurality of partition plates. These partition plates 3 divides the spacing between the porous material 1 and the back wall 4 vertically or obliquely to provide air layers 2 so that cells 10 are constituted by the porous material 1, back wall 4, and partition plates 3. The air layers 2 defined within the respective cells 10 may be filled with a porous sound-absorbent material such as glass wool.

Each of the cells 10, surrounded by the partition plates 3, has an oscillation plate 6 arranged for being driven by an oscillation-plate driving unit 5. Sound-pressure detectors 7 are arranged in the vicinity of the surface porous material 1 so that a detected signal is inputted to a signal-processing unit 8 where the signal is processed to drive the oscillation-plate driving unit 5.

In the first embodiment thus constructed, a sound-pressure signal detected in the cell 10 is inputted to the signal processing unit 8 where it is subjected to signal processing for causing oscillation of the oscillation plate 6 by the oscillation-plate driving unit 5. The output of the oscillation-plate driving unit 5 is controlled to cause the sound-pressure detector to near of its value unlimitedly to “zero”.

Meanwhile, it is preferred that the porous material 1 on the surface has flow resistance close to ρ C, where ρ is density and C is sound velocity. The porous material 1 may be formed by a porous sound-absorbent material or the like to increase the thickness thereof. The oscillation plate 6 combined with the oscillation driver 5 may be formed by a usual voice-coil type speaker, a piezo-electric device, a piezo-electric film, or the like.

The signal processing unit 8 may be either the analog type or the digital type, though feed-back control is applied in the present case. The feedback control has to be made to increase the gain to a possibly large value, in order to avoid entering into a region where oscillation is caused under a positive feed-back on a one-loop transfer function G for the system, in which system the sound-pressure detector 7 detects sound pressure which was acoustically radiated by oscillation by the oscillation plate 6 to transmit a signal from the sound-pressure detector 7 via the signal processing unit 8, and oscillation-plate driving unit 5. It is also possible to apply to the present control such various active noise-control signal processing techniques that the sound-pressure detecting signal is replaced as an error signal.

Figure 2:
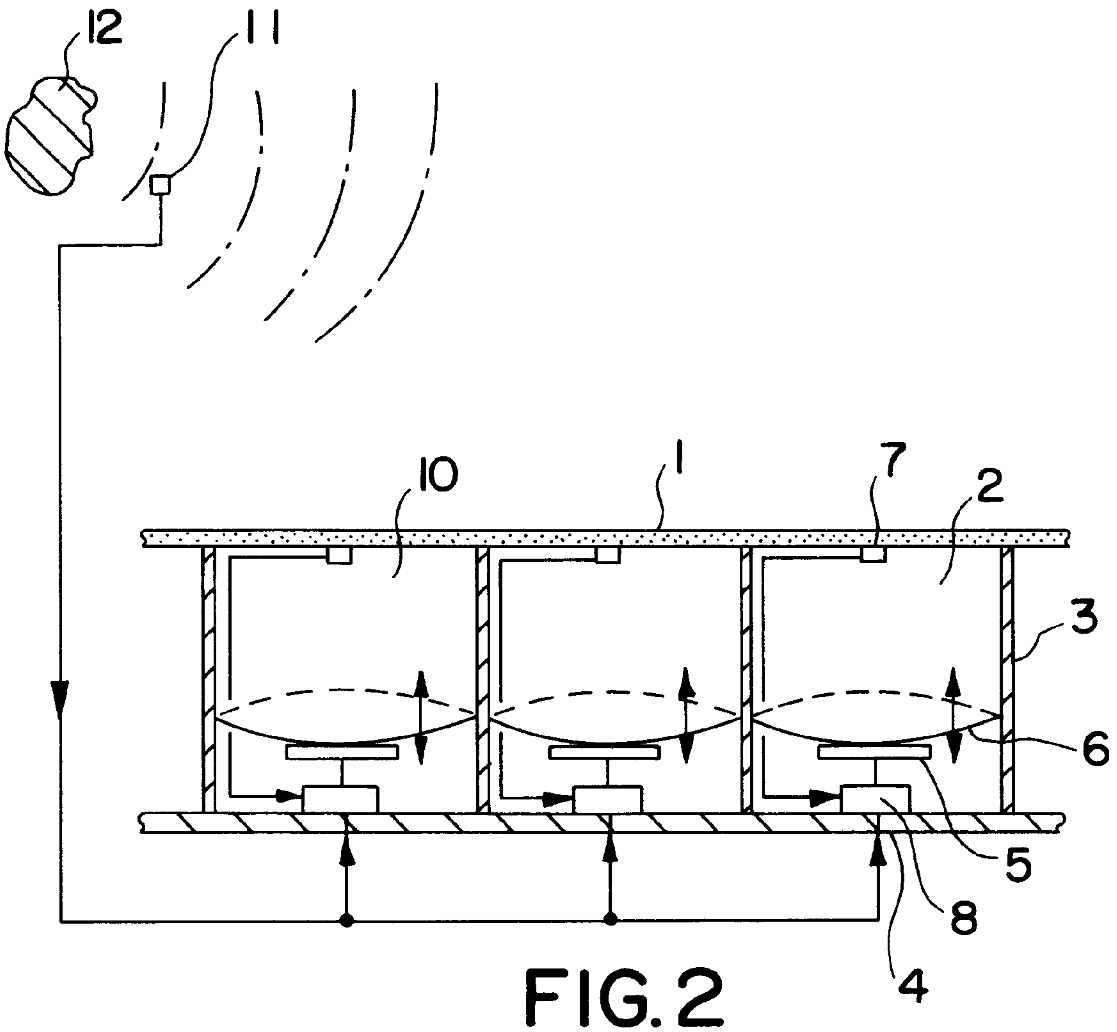
FIG. 2 is an structural view of an active acoustic wall according to a second embodiment of the invention.

FIG. 2 is a structural view of an active acoustic wall according to a second embodiment of the invention. The second embodiment has a structure including a reference-signal detector 11 which is added to the first embodiment shown in FIG. 1. This embodiment is applicable to cases where a sound source for an acoustic wall is clarified beforehand or a coming sound wave is detectable on the upstream side thereof. The reference-signal detector 11 is provided to detect a signal from a sound source 12, and a detected signal is inputted to a signal processing unit 8 where control is done similarly to the first embodiment while referring to the signal, thereby realizing accurate sound absorption.

The second embodiment performs feed-forward control with using as an error signal a signal detected by the sound-pressure detector 7, to which signal-control techniques concerning active noise control such as a Filtered-X-LMS can be applied.

Figure 3:
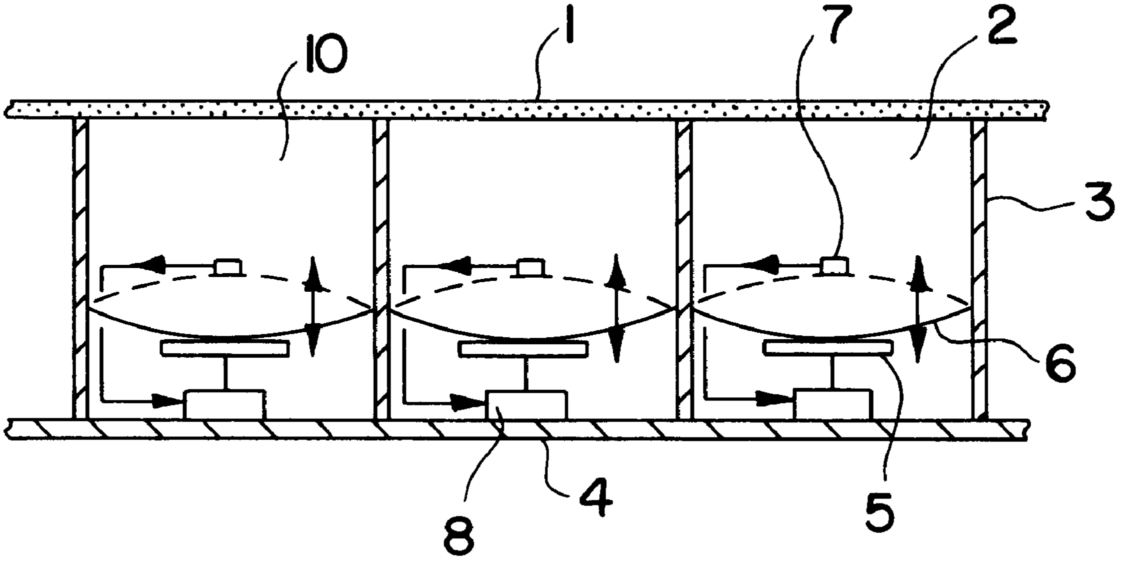
FIG. 3 is an structural view of an active acoustic wall according to a third embodiment of the invention.

FIG. 3 is a structural view of an active acoustic wall according to a third embodiment of the invention. The third embodiment has the same structure as that of the first embodiment, except for the location of the sound-pressure detector 7. The sound-pressure detector 7 is placed immediately in front of the oscillation plate 6.

In the third embodiment thus constructed, the sound-pressure detector 7 is arranged immediately in front of the oscillation plate 6, as mentioned above, so that a signal detected is delivered to a signal processing unit 8. The signal processing unit 8 adjust a one-loop transfer function G to near −1 (gain 1, phase inverted) as close as possible. In the transfer function G, transfer is made from the sound-pressure detector 7 via the signal-processing unit 8 and the oscillation plate 6 where sound pressure is acoustically radiated for being detected by the sound-pressure detector 7.

In this case, the air layer 2 may be filled with an acoustic material and wherein partition plates 3 is omitted. However, it is preferred to decrease small the flow resistance on a surface of a porous material or a sound-absorbent material. The oscillation plate 6 combined with the oscillation driving unit 5 may be something alike an ordinary voice-coil type speaker or a piezo-electric device or film. The sound-pressure detector 7 may be arranged separately from the oscillation plate 6 as shown in FIG. 3 or incorporated therein. The circuit of the signal-processing unit 8 may be of a digital or a analog type.

Figure 4:
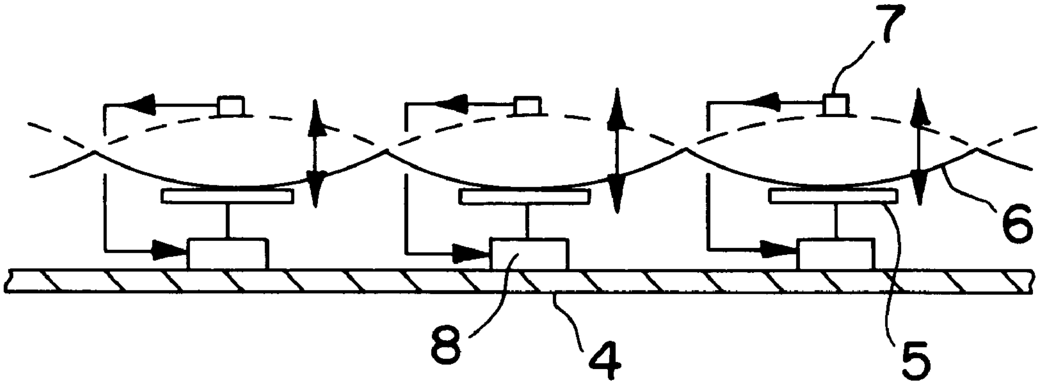
FIG. 4 is an structural view of an active acoustic wall according to a fourth embodiment of the invention.

FIG. 4 is a structural view of an acoustic wall according to a fourth embodiment of the invention. The fourth embodiment has a structure in which the surface porous material 1 as well as partition plates 3 are removed off from the acoustic wall of the third embodiment of FIG. 3. In this example, however, the partition plates 3 may solely be left provided. The operation of the fourth embodiment thus constructed is similar to that of the third embodiment, and explanations thereon being omitted.

Figure 5:
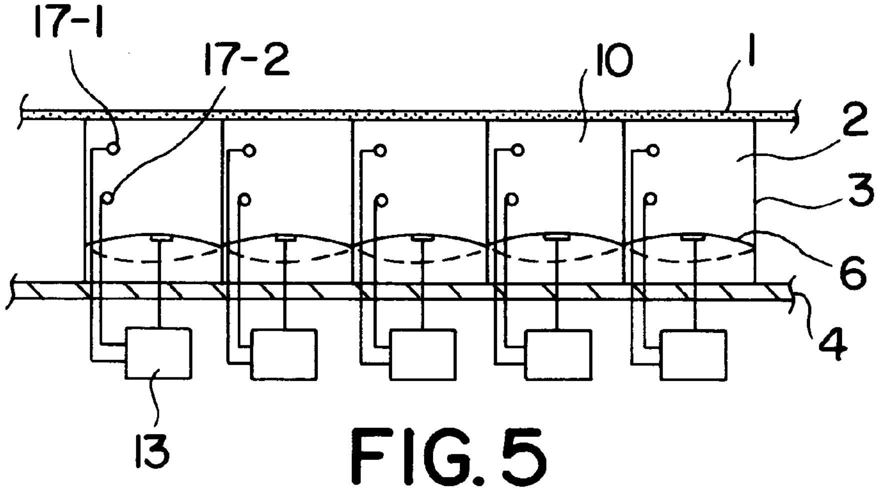
FIG. 5 is an structural view of an active acoustic wall according to a fifth embodiment of the invention.

FIG. 5 is a structural view of an active acoustic wall according to a fifth embodiment of the invention. In FIG. 5, an active acoustic wall has a porous material 1 in an surface thereof, 4 is a back wall, 3 is a plurality of partition plates. The partition plates 3 divide the spacing between the porous material 1 and the back wall 4 perpendicularly or obliquely to provide air layers 2 so that cells 10 are defined by the porous material 1, back wall 3, and the partition plates 3. The cell 10, surrounded by the partition plates 6, have respective oscillation plates 6 arranged therein. The air layers 2 of cells each include a two sound-pressure detectors 17-1, 17-2 arranged perpendicular relative to the back wall 4, to thereby provide an output to an input terminal of a controller 13.

The controller 13 calculates the reflectivity or the surface impedance of a sound wave, from the output of the two acoustic detector 17-1, 17-2. The controller then compares the calculation value with a predetermined optimal value to output a control signal for oscillating the oscillation plate 6 such that the calculated value nears the optimal value.

In this case, the controller 13 performs feed-back control such that the reflectivity obtained from the two sound-pressure detectors 17-1, 17-2 is brought to an optimal value. However, when a sound source is clarified beforehand, it is possible to detect a waveform at the sound source to carry out feed-back control using a detection result as a reference signal.

Figure 6:
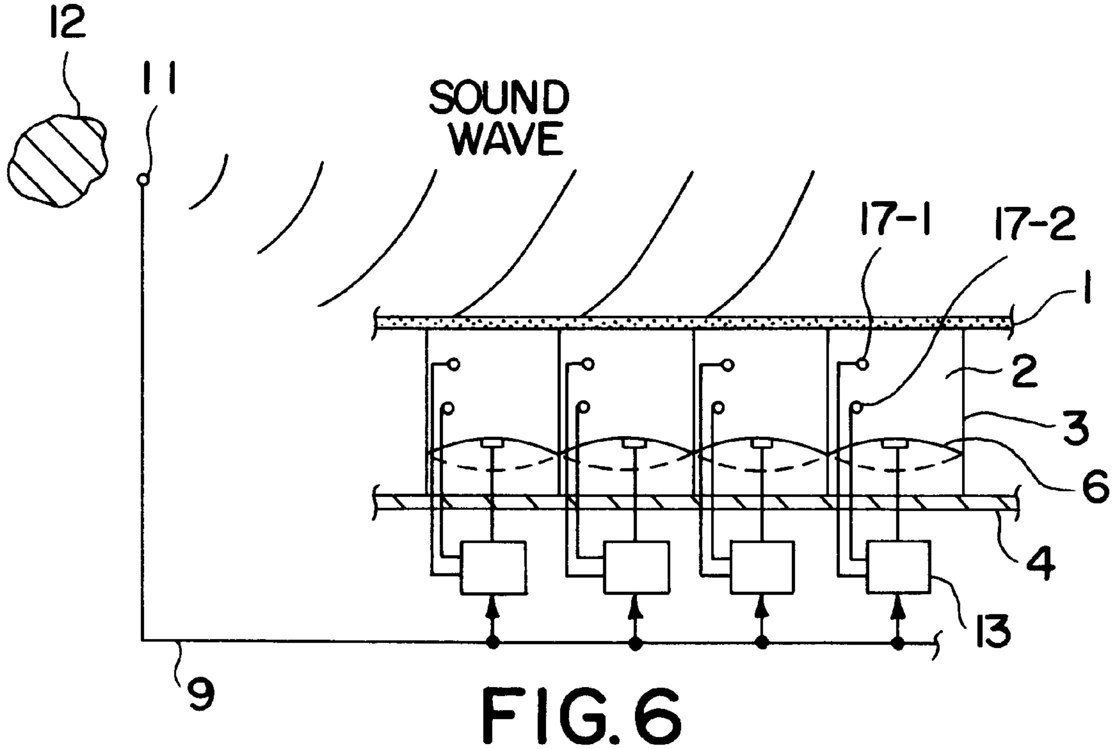
FIG. 6 is an structural view of an active acoustic wall according to a sixth embodiment of the invention.

FIG. 6 is a structural view of an active acoustic wall according to a sixth embodiment of the invention, which adopts the above-mentioned control. In FIG. 6, the structure of the arrangement is similar to that of the fifth embodiment of FIG. 5, except for an addition of a system which detects a sound source 12 by a reference-signal detector 11 for inputting a reference signal 9 to a controller 13.

With such arrangement, this embodiment performs detection of a waveform from the sound source 12 previously known by using a reference-signal detector 11, so that the reference signal 9 is fed back to the controller 13. The controller 13 makes reference to the reference signal 9 to perform control in a manner similar to the fifth embodiment, thereby making possible accurate sound absorption.

Figure 7:
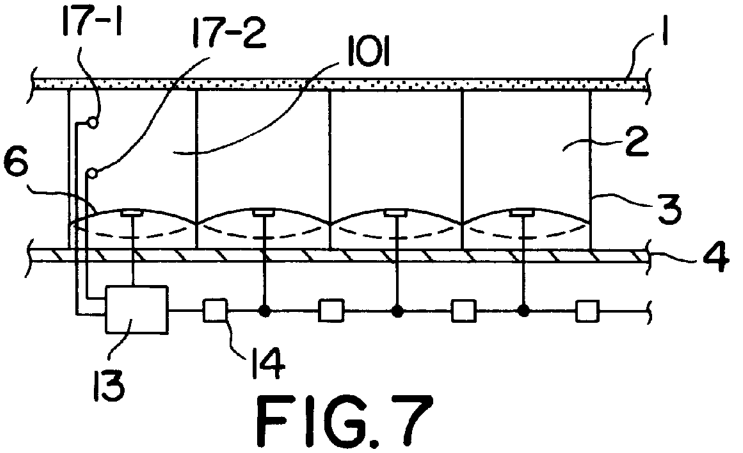
FIG. 7 is an structural view of an active acoustic wall according to a seventh embodiment of the invention.

FIG. 7 is a structural view of an active acoustic wall according to a seventh embodiment of the invention. In the above fifth and sixth embodiments, the oscillation plates 6 are controllably operated in respective cells 10 defined between the partition plates 3. However, when the incident direction of a sound wave is clarified, it is possible to perform control on all the cells by using a sole signal for a representative cell. In FIG. 7, sound-pressure detector 17-1, 17-2 are arranged in only a representing cell 101 to input a signal to a controller 13, to thereby provide respectively delays through delay circuits 14 for controlling the oscillation of oscillation plates 6 within the cells.

Figure 8:
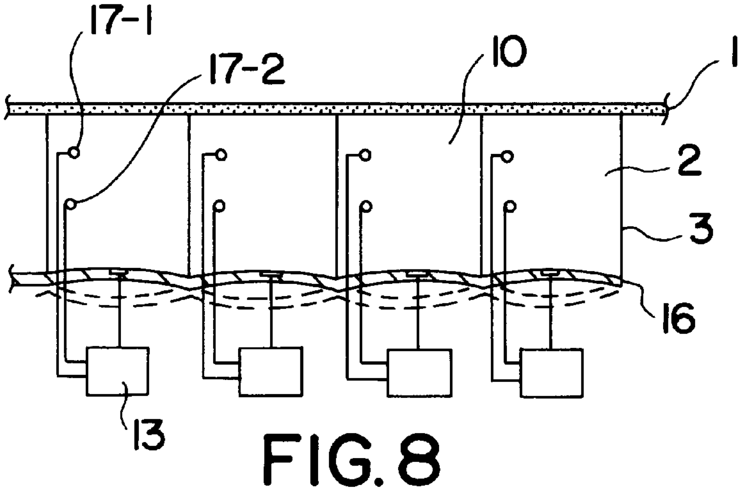
FIG. 8 is an structural view of an active acoustic wall according to an eighth embodiment of the invention.

FIG. 8 is a structural view of an active acoustic wall according to an eighth embodiment of the invention. The structure of FIG. 8 is different from that of FIG. 5 in that a back wall 16 is directly oscillated therein instead of oscillation of the oscillation plate 6 within the cells 10. The structure in respect of other points is similar to FIG. 5 to allow alike control.

Figure 9:
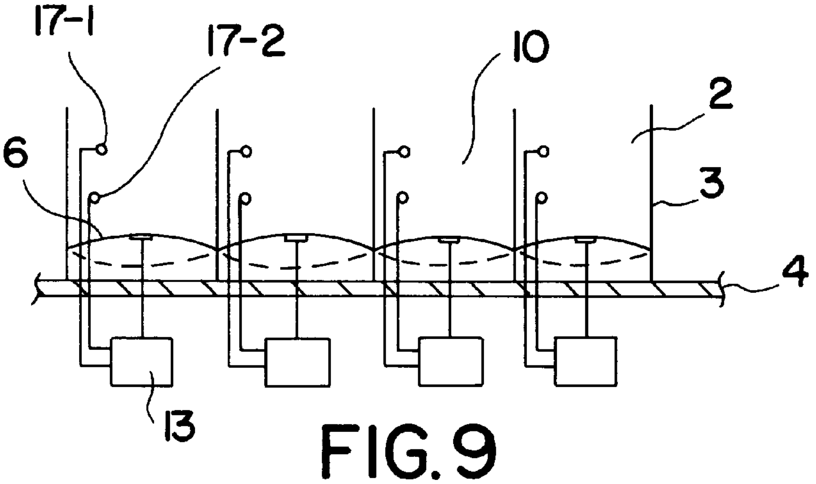
FIG. 9 is an structural view of an active acoustic wall according to a ninth embodiment of the invention.

FIG. 9 is a structural view of an active acoustic wall according to ninth embodiment of the invention. As shown in FIG. 9, this embodiment presents a case where a porous material 1 is omitted from a surface thereof. That is, sound absorption is made in air layers 2 defined by partition plates 3 in a manner similar to the case of FIG. 5.

Figure 10:
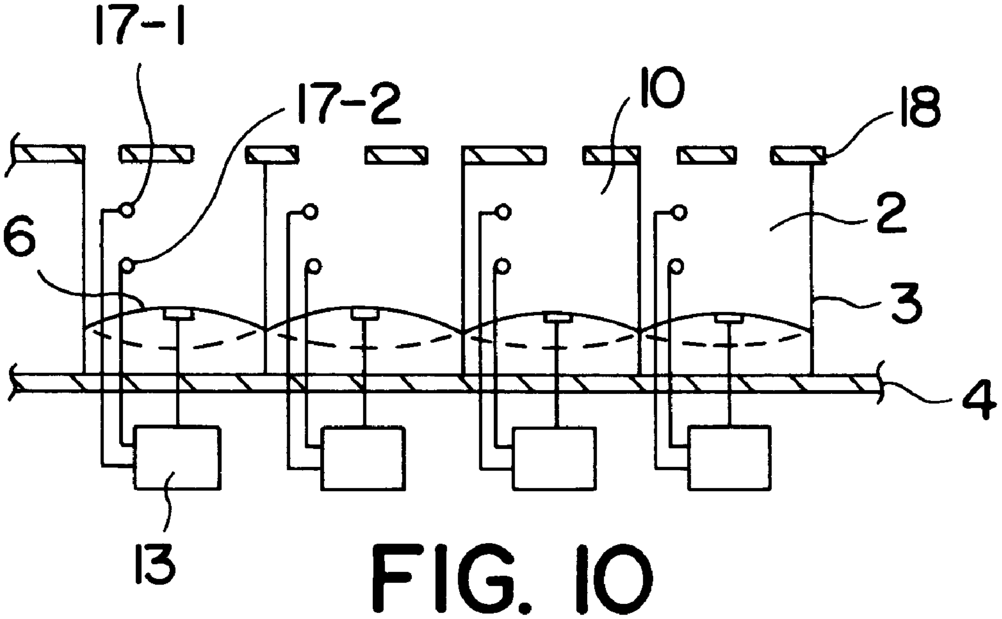
FIG. 10 is an structural view of an active acoustic wall according to a tenth embodiment of the invention.

FIG. 10 is a structural view of an active acoustic wall according to a tenth embodiment of the invention. As shown in FIG. 10, this embodiment is similar to the structure of fifth embodiment of FIG. 5 excepting that the a perforated plate 18 is employed in place of the surface porous material 1 of FIG. 5.

Figure 11:
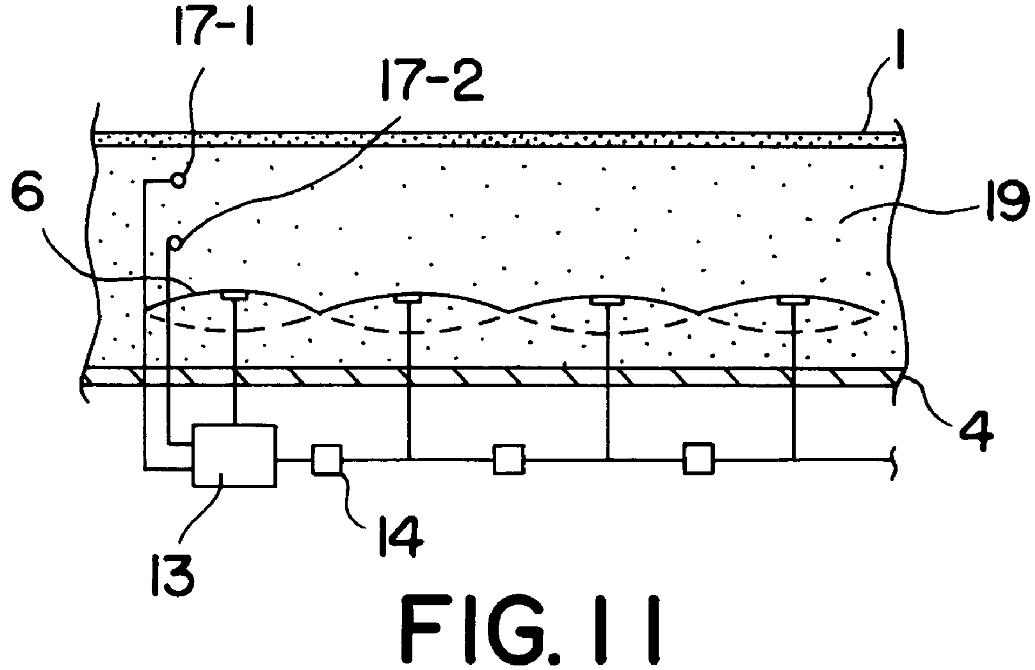
FIG. 11 is an structural view of an active acoustic wall according to an eleventh embodiment of the invention.
Figure 12:
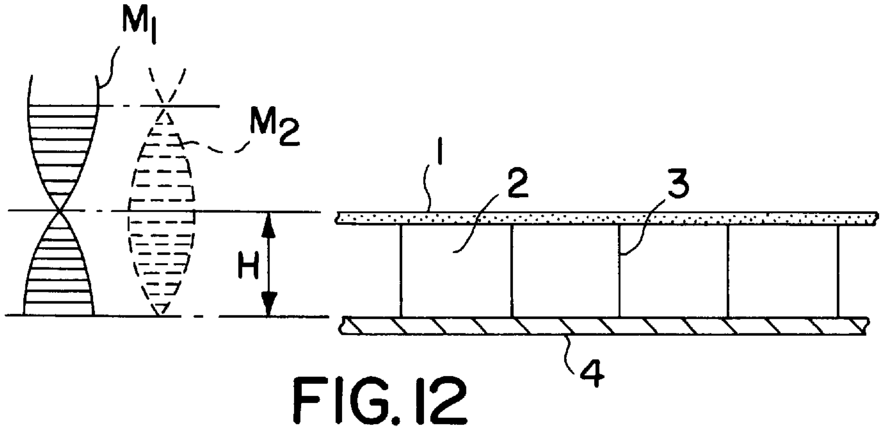
FIG. 12 is an explanatory view concerning a sound-pressure mode and a particle-velocity mode for the active acoustic wall of the first and second embodiments of the invention.
Figure 13:
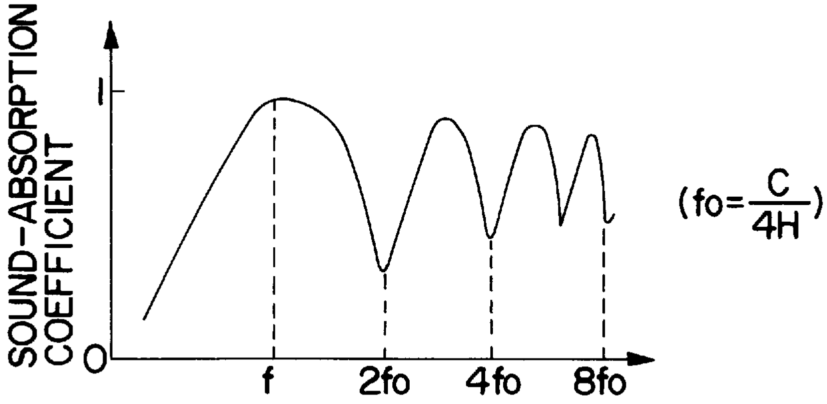
FIG. 13 is a graph showing a relation between frequencies and sound-absorption coefficients for the first and second embodiments of the invention.
Figure 14:
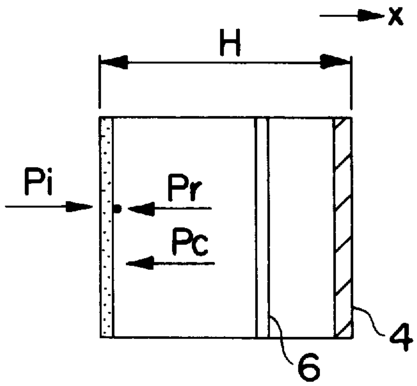
FIG. 14 is an explanatory view concerning incidence, reflection, radiation of sound pressure for the first and second embodiments of the invention.
Figure 15:
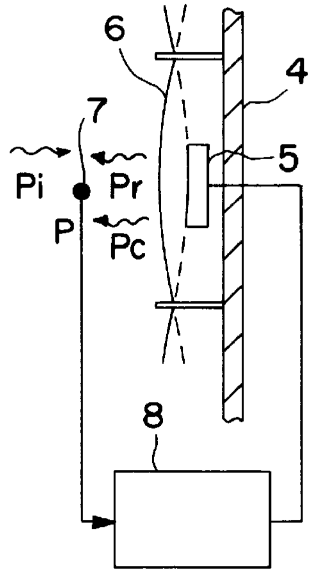
FIG. 15 is an explanatory view concerning the operation of the active acoustic wall for the third and fourth embodiments of the invention.
Figure 16:
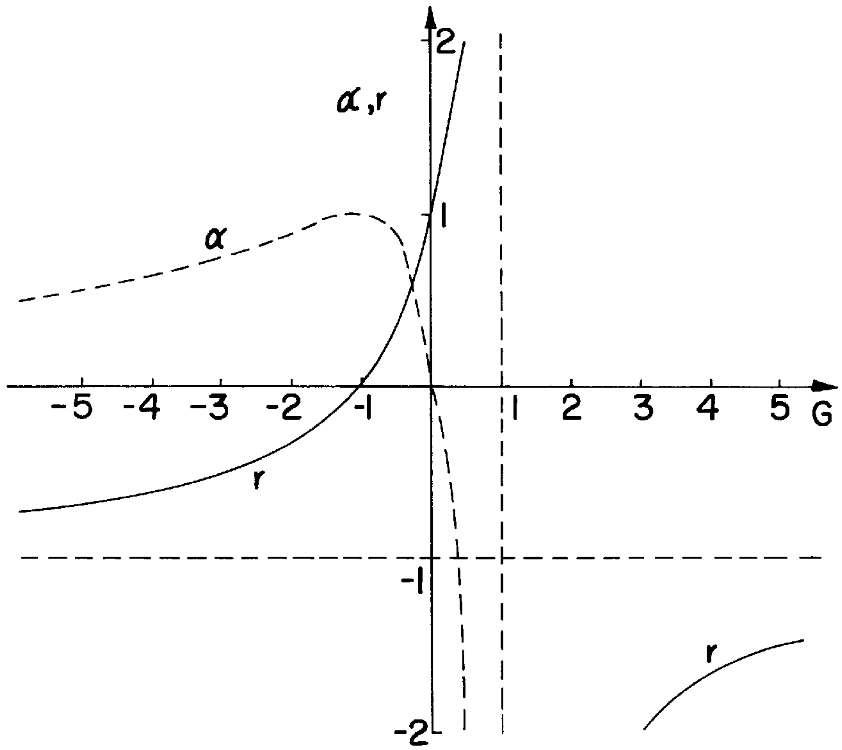
FIG. 16 is a graph showing relations between a transmission function, a sound-absorption coefficient, and reflectivity for the third and fourth embodiments of the invention.

FIG. 11 is a structural view of an active acoustic wall according to an eleventh embodiment of the invention. This embodiment has a structure similar to that of the seventh embodiment of FIG. 7 excepting that a sound-absorbent material 19 is filled in the air layers 2 with the partition plates 3 eliminated.

Figure 17A:
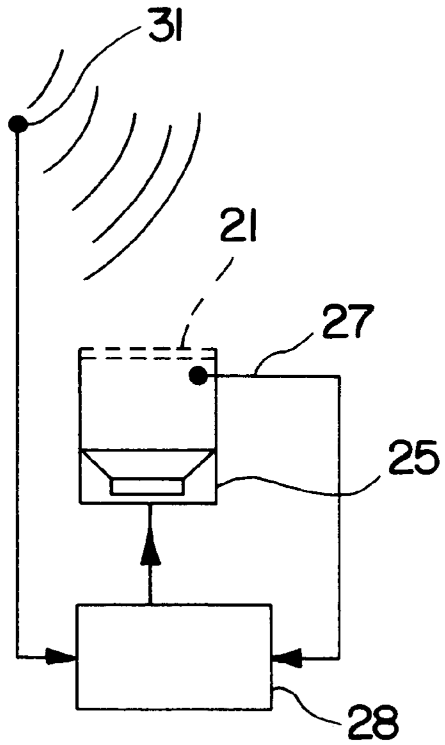
FIG. 17 are diagrams showing the effects by the first and second embodiment of the invention, wherein (a) is a diagram of the arrangement of an acoustic wall, and (b) is a diagram showing the relation between frequencies and sound-absorption coefficients.
Figure 17B:
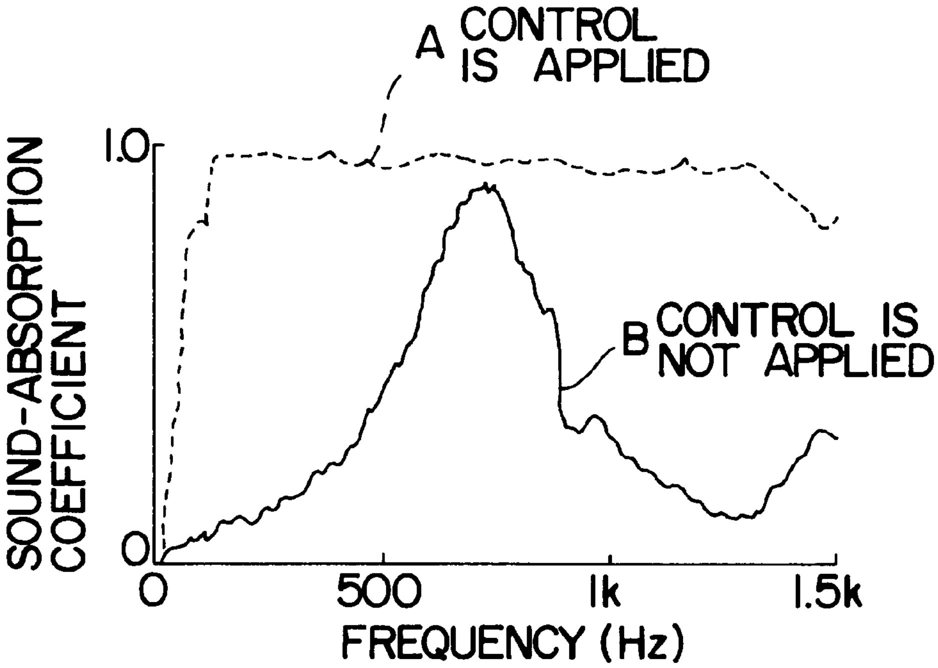

FIG. 17 is a diagrams for showing effects of the acoustic wall according to the first and second embodiments of the invention. (a) of FIG. 17 is a configulative diagram for examining effects of the acoustic walls, whereas (b) shows the sound-absorption coefficient for each frequency-band. As shown in (a) of the figure, a speaker 25 is provided on the back side of a porous material 21 with an error-compensating microphone 27 placed in the vicinity of the back of the porous material 21. A signal detected by the error-compensating microphone 27 is inputted to a control unit 28 in addition to inputting thereto of a signal detected by a reference-signal detecting microphone 31, for controlling the sound due to oscillation by the speaker 25. The sound-absorption coefficient is examined in a frequency band ranging from 8 to 1.5 kHz.

It will be understood that the noise-absorption coefficient is better in A than B over the entire frequency range, as shown in FIG. 17(*b*), wherein the control according to the invention is applied to A while not applied to B.

Figure 18A:
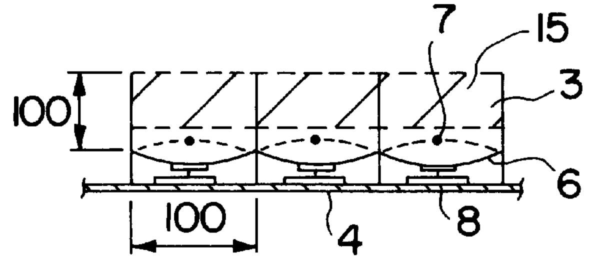
FIG. 18 are diagrams showing effects by the third and fourth embodiments of the invention, wherein (a) is a diagram of the arrangement of an acoustic wall, and (b) is a diagram showing the relation between frequencies and sound-absorption coefficients.
Figure 18B:
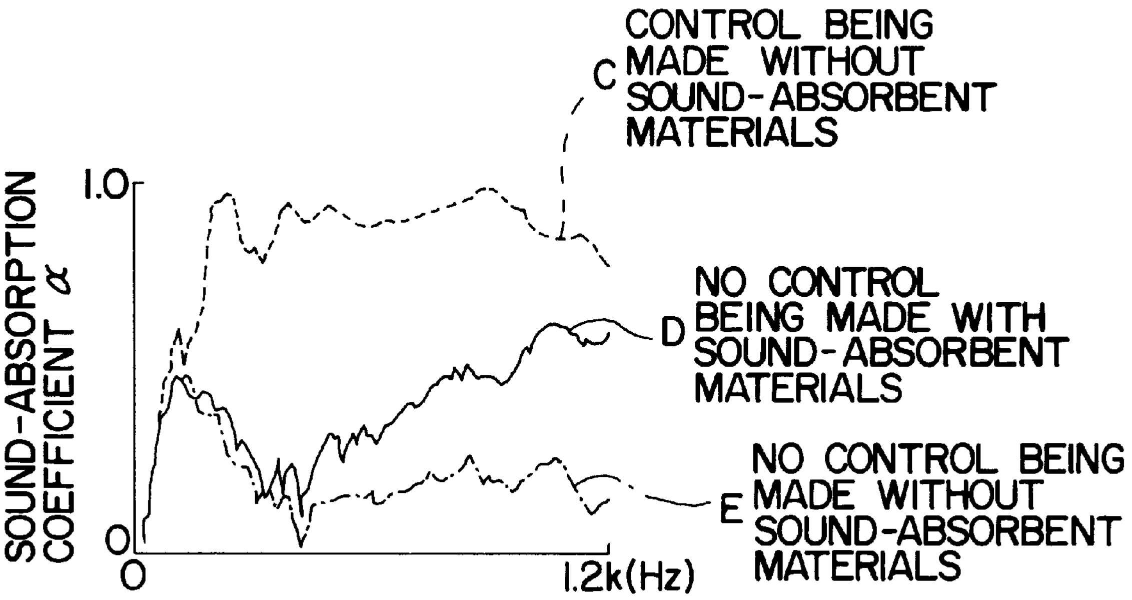

FIG. 18 is a diagrams for showing effects of the acoustic wall according to the third and fourth embodiments of the invention. (a) of the figure is a configulative diagram for examining effect of the acoustic wall, whereas (b) shows a sound-absorption coefficient for each frequency-band. As shown in (a), a back wall 4 is divided by partition plates 3 at a pitch of 100 mm to define 100 mm-square cells, sound-absorbent materials 15 are placed in respective cells at a top as viewed in the figure, and sound-pressure detectors 7 are respectively placed close to oscillation plates 6 so that a signal detected is inputted to a corresponding signal-processing unit 8 to perform control of the oscillation plates 6. The sound-absorption coefficient is examined in a frequency band ranging from 0 to 1.5 kHz, as shown in (b) of the figure.

In FIG. 18(*b*), C is a case where control is made without the sound-absorbent materials 15, D a case where the sound-absorbent materials 15 are provided but no control is made, and E a case where no sound-absorbent materials 15 are used and no control is made. It is understood that the noise-absorption coefficient is greatly improved by the acoustic wall as provided in the third and fourth embodiment.

Figure 19:
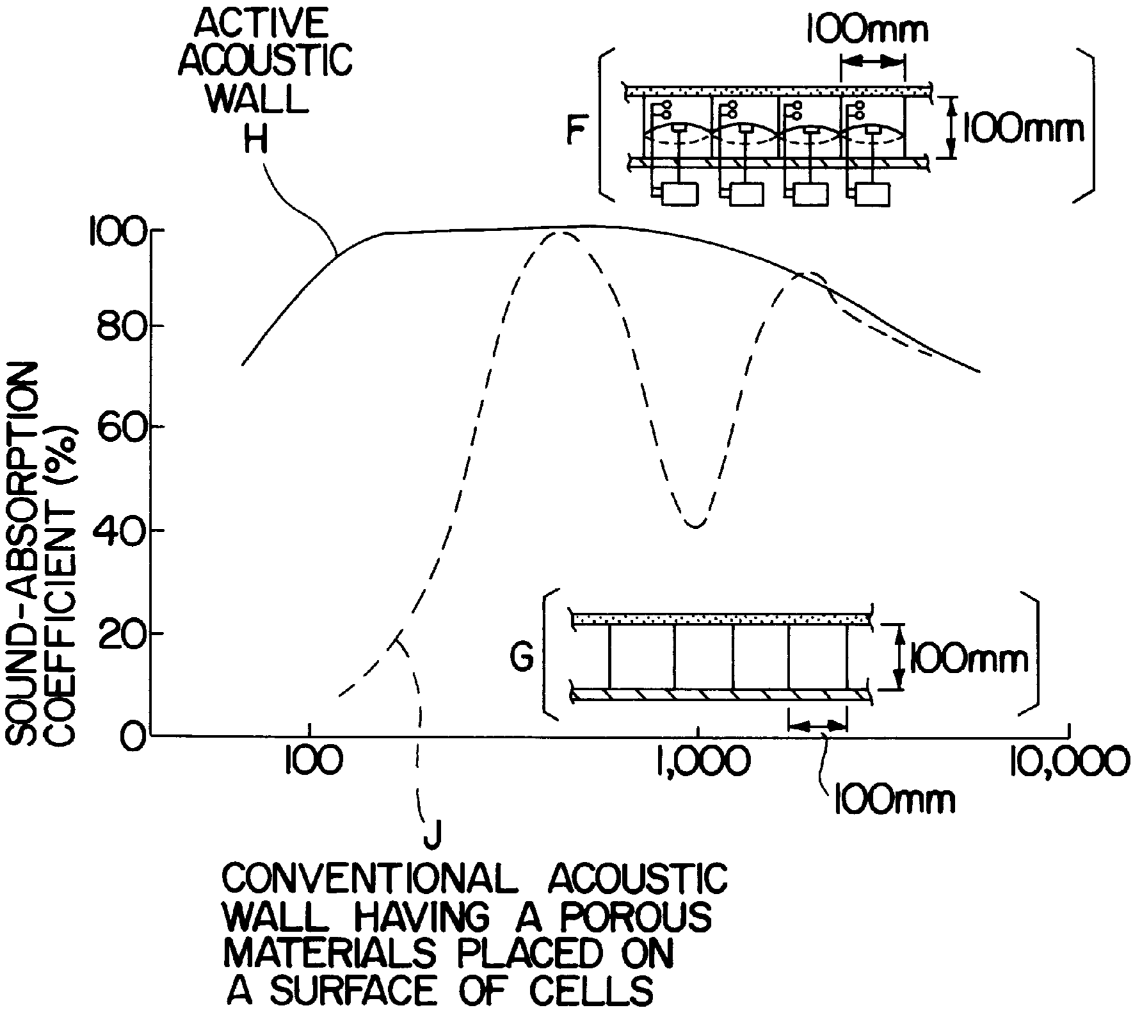
FIG. 19 is a diagram showing effects by the fifth to eleventh embodiments of the invention.
Figure 20:
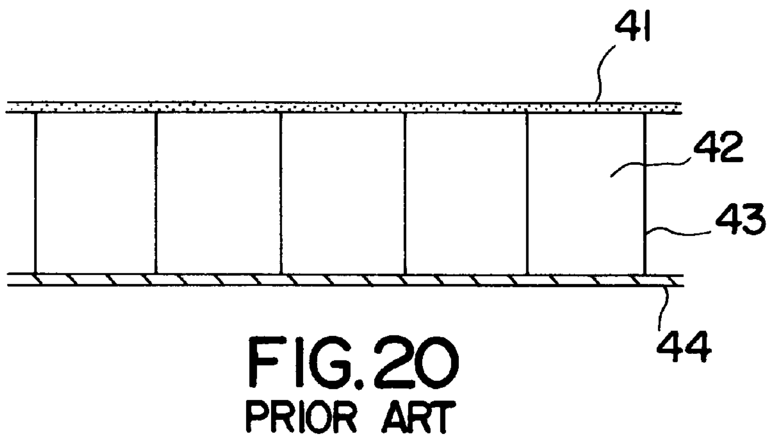
FIG. 20 PRIOR ART
FIG. 20 is a structural view of a conventional acoustic wall having a porous material provided on a surface thereof.
Figure 21:
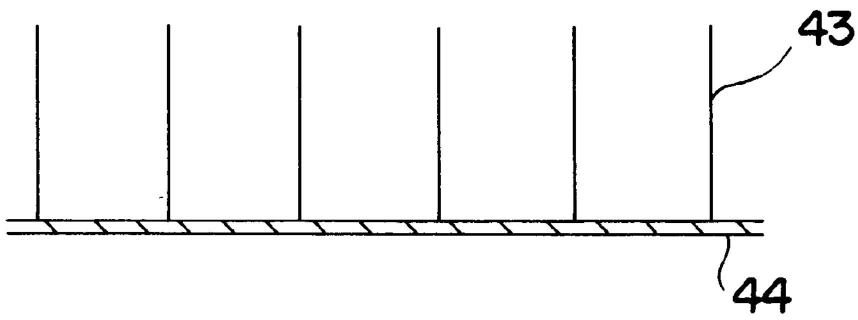
FIG. 21 PRIOR ART
FIG. 21 is a structural view of a conventional acoustic wall having openings in a surface thereof.
Figure 22:
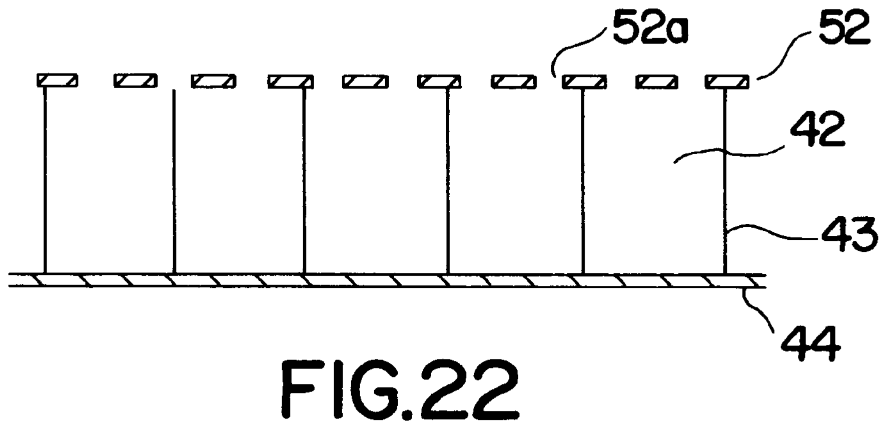
FIG. 22 PRIOR ART
FIG. 22 is a structural view of a conventional acoustic wall having a perforated plate in a surface thereof.
Figure 23:
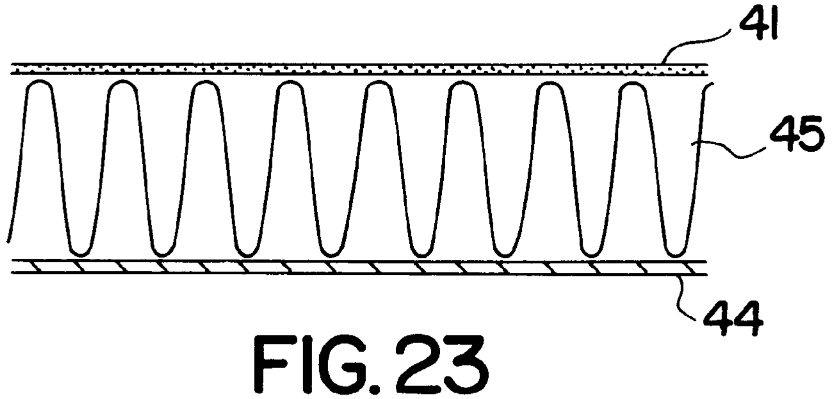
FIG. 23 PRIOR ART
FIG. 23 is a structural view of a conventional acoustic wall having a sound-absorbent material contained in the interior thereof.

FIG. 19 is a diagram showing effects of the acoustic walls according to the fifth to eleventh embodiments of the invention, which provides the relation between the frequency and the sound-absorption coefficient. In the figure, J shows a characteristic for the conventional acoustic wall, as shown by G, having a porous material placed on a surface of cells with a size 100 mm by 100 mm, whereas H provides a characteristic for the acoustic walls of the invention, as shown by F, each constituted by the 100 mm-by-100 mm cells, the control units, the oscillation plates, and two sound-pressure detectors. From the comparison between the characteristics J and H, it is possible, for the characteristic H of this invention to obtain, by using the thin acoustic walls, a high sound absorption coefficient over a low-to high wide frequency range.

What is claimed is:

1. An active acoustic wall for absorbing sound waves across a broadband frequency range, comprising:

a perforated plate comprising at least one selected from the group consisting of a perforated member and a porous material, said perforated plate having a front side and a back side;

a back wall spaced from said back side of said perforated plate such that a space is formed between said back side of said perforated plate and said back wall;

a plurality of partition plates dividing said space between said perforated plate and said back wall into a plurality of sections;

oscillation plates provided within each of said sections, respectively;

driving units for driving said oscillation plates;

two sound pressure detectors provided within each of said sections providing first and second signals; and a signal processing unit connected with said sound pressure detectors and said driving units, receiving each of said first and second signals, calculating the impedance of each of said sections, comparing the impedance to a predetermined value, and providing an output signal to each of said driving units such that each of said oscillation plates oscillates and creates an impedance which approximates said predetermined value.

2. The wall of claim 1, wherein said signal processor unit calculates the impedance of each of said sections by separating an incident sound wave from a reflecting sound wave and measuring said respective sound waves.

3. The wall of claim 1, wherein said plurality of sections have absorption materials filled therein.

4. The wall of claim 2, wherein said signal processing means controls the oscillation of each of said oscillation plates such that the difference between said reflecting sound wave and said incident sound wave approximates to a minimum.

5. The wall of claim 3, wherein said signal processing unit controls the oscillation of each of said oscillation plates such that a characteristic of a one loop transfer function, in which transfer is made through sound pressure generated by oscillation of each of said oscillation plates to the output of said sound pressure detectors, approximates to −1.

6. The wall of claim 1, wherein said oscillation plates and said back wall are integrally formed.

7. An active acoustic wall, comprising:

a perforated plate comprising at least one selected from the group consisting of a perforated member and a porous material, said perforated plate having a front side and a back side;

a back wall spaced from said back side of said perforated plate such that a space is formed between said back side of said perforated plate and said back wall;

wherein said space is a continuous space between said back wall and said perforated plate, said space comprising a plurality of sections that are open to each other;

oscillation plates provided within respective said sections;

driving units for driving said oscillation plates;

two sound pressure detectors within each of said sections for providing first and second signals; and a signal processing unit, connected with said sound pressure detectors and said driving units, for receiving each of said first and second signals, calculating the impedance of each of said sections, comparing the impedance to a predetermined value, and providing an output signal to each of said driving units such that each of said oscillation plates oscillates and creates an impedance which approximates said predetermined value.

8. The wall of claim 7, wherein said signal processor unit calculates the impedance of each of said sections by separating an incident sound wave from a reflecting sound wave and measuring said respective sound waves.

9. The wall of claim 8, wherein said signal processor unit controls oscillation of each of said oscillation plates such that the difference between said reflecting sound wave and said incident sound wave approximates to a minimum.

10. The wall of claim 7, wherein said plurality of sections have absorption materials filled therein.

11. The wall of claim 8, wherein said oscillation plate and said back wall are integrally formed.

12. The wall of claim 7, wherein said signal processing unit controls the oscillation of each of said oscillation plates such that a characteristic of a one loop transfer function, in which transfer is made through sound pressure generated by oscillation of each of said oscillation plates to the output of said sound pressure detectors, approximates to −1.

13. An active acoustic, comprising:

a back wall forming a space on one side thereof, wherein said space comprises a plurality of sections;

oscillation plates provided within respective said sections;

driving units for driving said oscillation plates;

two sound pressure detectors within each of said sections for providing first and second signals; and a signal processing unit connected with said sound pressure detectors and said driving units receiving each of said first and second signals and calculating the impedance of each of said sections and comparing the impedance to a predetermined value and providing an output signal to each of said oscillation plates such that each of said oscillation plates oscillates and creates an impedance which approximates said predetermined value.

14. The wall of claim 13, wherein said signal processor unit calculates the impedance of each of said sections by separating an incident sound wave from a reflecting sound wave and measuring said respective sound waves.

15. The wall of claim 14, wherein said signal processor controls oscillation of each of aid oscillation plates such that the difference between said reflecting sound wave and said incident sound wave approximates to a minimum.

16. The wall of claim 13, wherein said plurality of sections have absorption materials filled therein.

17. The wall of claim 13, wherein said oscillation plate and said back wall are integrally formed.

18. The wall of claim 13, and further comprising a plurality of partition plates dividing said space into said plurality of sections.

19. The wall of claim 13, wherein said signal processing unit controls the oscillation of each of said oscillation plates such that a characteristic of a one loop transfer function, in which transfer is made through sound pressure generated by oscillation of each of said oscillation plates to the output of said sound pressure detectors, approximates to −1.

20. An active acoustic wall, comprising:

a perforated plate comprising at least one selected from the group consisting of a perforated member and a porous material, said perforated plate having a front side and a back side;

a back wall spaced from said back side of said perforated plate such that a space is formed between said back side of said perforated plate and said back wall;

a plurality of partition plates dividing said space between said perforated plate and said back wall into a plurality of sections;

oscillation plates respectively provided within each of said sections;

driving units for driving said oscillation plates;

two sound pressure detectors provided within one of said sections for providing first and second signals; and a signal processing unit connected with said sound pressure detectors and said driving units for receiving said first and second signals, calculating the impedance of said one of said sections, comparing the impedance to a predetermined value, and providing a sole output signal to each of said driving units such that each of said oscillation plates oscillates and creates an impedance which approximates said predetermined value.

21. The wall of claim 20, wherein said signal processor unit delays providing said sole output signal to each said driving unit.

22. The wall of claim 20, wherein said signal processor calculates the impedance of each of said sections by separating an incident sound wave from a reflecting sound wave and measuring said respective sound waves.

23. The wall of claim 21, wherein said signal processor controls oscillation of each of said oscillation plates such that the difference between a reflecting sound wave and an incident sound wave approximates to a minimum.

24. The wall of claim 22, wherein said signal processor controls oscillation of each of said oscillation plates such that the difference between a reflecting sound wave and an incident sound wave approximates to a minimum.

25. The wall of claim 20, wherein said signal processor further comprises delay circuits for controlling the oscillation of said oscillation plates.

26. The wall of claim 20, wherein said plurality of sections have absorption materials filled therein.

27. The wall of claim 20, wherein said oscillation plates and said back wall are integrally formed.

28. The wall of claim 20, wherein said signal processing unit controls the oscillation of each of said oscillation plates such that a characteristic of a one-loop transfer function, in which transfer is made through a sound pressure generated by the oscillation of each of said oscillation plates to the output of said sound pressure detectors, approximates to −1.

29. An active acoustic wall for absorbing sound waves across a broadband frequency range, comprising:

a perforated plate comprising at least one selected from the group consisting of a perforated member and a porous material, said perforated plate having a front side and a back side;

a back wall spaced from said back side of said perforated plate such that a space is formed between said back side of said perforated plate and said back wall;

a plurality of partition plates dividing said space between said perforated plate and said back wall into a plurality of sections;

oscillation plates integral with said back wall, one of said oscillation plates being provided within each of said sections, respectively;

driving units for driving said oscillation plates;

sound pressure detectors respectively provided at a desired location within said sections for detecting sound pressure at the desired location within said sections; and a signal processing unit for each of said sections and connected with a respective one of said sound pressure detectors and one of said driving units, said signal processing unit independently controlling the respective one of said driving units, and thus a respective one of said oscillation plates, such that sound absorption at a specified location is made across a low to high frequency range based on output from said sound pressure detectors;

wherein said plurality of sections have absorption materials filled therein; and wherein two of said sound pressure detectors are provided within each said section for separating an incident sound wave from a reflecting sound wave and measuring said waves, respectively, and wherein said signal processing unit controls the oscillation of each of said oscillation plates such that reflectivity of the sound wave calculated on the basis of the output from said two sound pressure detectors approximates to a predetermined value.

30. An active acoustic wall for absorbing sound waves across a broadband frequency range, comprising;

a perforated plate comprising at least one selected from the group consisting of a perforated member and a porous material, said perforated plate having a front side and a back side;

a back wall spaced from said back side of said perforated plate such that a space is formed between said back side of said perforated plate and said back wall;

a plurality of partition plates dividing said space between said perforated plate and said back wall into a plurality of sections;

oscillation plates integral with said back wall, one of said oscillation plates being provided within each of said sections, respectively;

driving units for driving said oscillation plates;

sound pressure detectors respectively provided at a desired location within said sections for detecting sound pressure at the desired location within said sections; and a signal processing unit for each of said sections and connected with a respective one of said sound pressure detectors and one of said driving units, said signal processing unit independently controlling the respective one of said driving units, and thus a respective one of said oscillation plates, such that sound absorption at a specified location is made across a low to high frequency range based on output from said sound pressure detectors;

wherein said plurality of sections have absorption materials filled therein;

wherein two sound pressure detectors are provided within each said section for separating an incident sound wave from a reflecting sound wave and measuring said waves, respectively, and wherein said signal processing unit controls the oscillation of each of said oscillation plates such that reflectivity of the sound wave calculated on the basis of the output from said two sound pressure detectors approximates to a predetermined value.

31. An active acoustic wall for absorbing sound waves across a broadband frequency range, comprising:

a perforated plate comprising at least one selected from the group consisting of a perforated member and a porous material, said perforated wall having a front side and a back side;

a back wall spaced from said back side of said perforated plate such that a space is formed between said back side of said perforated plate and said back wall;

wherein said space is a continuous space between said back wall and said perforated plate, said space comprising a plurality of sections that are open to each other;

oscillation plates provided within respective said sections;

driving units for driving said oscillation plates;

sound pressure detectors respectively provided at a desired location within said sections for detecting sound pressure at the desired location within said sections; and a signal processing unit for each of said sections and connected with a respective one of said sound pressure detectors and one of said driving units, said signal processing unit independently controlling the respective one of said driving units, and thus a respective one of said oscillation plates, such that sound absorption at a specified location is made across a low to high frequency range based on output from said sound pressure detectors;

wherein two sound pressure detectors are provided within each said section for separating an incident sound wave from a reflecting sound wave and measuring said waves, respectively, and wherein said signal processing unit controls the oscillation of each of said oscillation plates such that reflectivity of the sound wave calculated on the basis of the output from said two sound pressure detectors approximates to a predetermined value.

32. An active acoustic wall for absorbing sound waves across a broadband frequency range, comprising:

a back wall forming a space on one side thereof, wherein said space comprises a plurality of sections;

oscillation plates provided within respective said sections;

driving units for driving said oscillation plates;

sound pressure detectors respectively provided at a desired location within said sections for detecting sound pressure at the desired location within said sections; and a signal processing unit for each of said sections and connected with a respective one of said sound pressure detectors and one of said driving units, said signal processing unit independently controlling the respective one of said driving units, and thus a respective one of said oscillation plates, such that sound absorption at a specified location is made across a low to high frequency range based on output from said sound pressure detectors;

wherein two sound pressure detectors are provided within each said section for separating an incident sound wave from a reflecting sound wave and measuring said waves, respectively, and wherein said signal processing unit controls the oscillation of each of said oscillation plates such that reflectivity of the sound wave calculated on the basis of the output from said two sound pressure detectors approximates to a predetermined value.

* * * * *